United States Patent
Pomrink et al.

(10) Patent No.: US 9,144,629 B2
(45) Date of Patent: *Sep. 29, 2015

(54) IONICALLY CROSSLINKED MATERIALS AND METHODS FOR PRODUCTION

(71) Applicant: NovaBone Products, LLC, Alachua, FL (US)

(72) Inventors: Gregory J. Pomrink, Newberry, FL (US); Cecilia A. Cao, Gainesville, FL (US); Joshua Clark, Alachua, FL (US); Zehra Tosun, Gainesville, FL (US); David C. Greenspan, Gainesville, FL (US); Srinivas Katta, Gainesville, FL (US)

(73) Assignee: NOVABONE PRODUCTS, LLC, Alachua, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/833,400

(22) Filed: Mar. 15, 2013

(65) Prior Publication Data

US 2014/0017281 A1    Jan. 16, 2014

Related U.S. Application Data

(63) Continuation-in-part of application No. 13/039,627, filed on Mar. 3, 2011, now Pat. No. 8,795,702.

(60) Provisional application No. 61/310,129, filed on Mar. 3, 2010, provisional application No. 61/710,332, filed on Oct. 5, 2012.

(51) Int. Cl.
| | |
|---|---|
| A61L 27/46 | (2006.01) |
| A61L 27/10 | (2006.01) |
| A61L 27/24 | (2006.01) |
| A61L 27/58 | (2006.01) |
| A61L 27/56 | (2006.01) |

(52) U.S. Cl.
CPC .................. *A61L 27/46* (2013.01); *A61L 27/24* (2013.01); *A61L 27/56* (2013.01); *A61L 2430/02* (2013.01)

(58) Field of Classification Search
CPC ..... A61L 27/46; A61L 2430/02; A61L 27/24; A61L 27/56; A61L 27/3633; A61L 27/365; A61L 27/446; A61L 27/025; A61K 33/42; A61K 38/39; A61K 45/06
See application file for complete search history.

(56) References Cited

U.S. PATENT DOCUMENTS

| | | | |
|---|---|---|---|
| 4,851,046 A | 7/1989 | Low et al. | |
| 5,320,844 A | 6/1994 | Liu | |
| 5,912,225 A | 6/1999 | Mao et al. | |
| 5,977,204 A | 11/1999 | Boyan et al. | |
| 6,027,742 A | 2/2000 | Lee et al. | |
| 6,045,555 A | 4/2000 | Smith et al. | |
| 6,153,212 A | 11/2000 | Mao et al. | |
| 6,166,173 A | 12/2000 | Mao et al. | |
| 6,187,047 B1 | 2/2001 | Kwan et al. | |
| 6,224,913 B1 | 5/2001 | Ducheyne et al. | |
| 6,238,687 B1 | 5/2001 | Mao et al. | |
| 6,306,169 B1 * | 10/2001 | Lee et al. ................... | 623/11.11 |
| 6,322,797 B1 | 11/2001 | Mao et al. | |
| 6,328,990 B1 | 12/2001 | Ducheyne et al. | |
| 6,344,496 B1 | 2/2002 | Niederauer et al. | |
| 6,395,036 B1 | 5/2002 | Czernuska et al. | |
| 6,413,538 B1 | 7/2002 | Garcia et al. | |
| 6,417,166 B2 | 7/2002 | Liu | |
| 6,569,466 B2 | 5/2003 | Ducheyne et al. | |
| 6,764,517 B2 | 7/2004 | Yamamoto et al. | |
| 6,902,584 B2 | 6/2005 | Kwan et al. | |
| 6,949,251 B2 | 9/2005 | Dalai et al. | |
| 6,969,501 B2 | 11/2005 | Sapieszko et al. | |
| 6,991,802 B1 | 1/2006 | Ahola et al. | |
| 6,991,803 B2 | 1/2006 | Sapieszko et al. | |
| 7,014,640 B2 | 3/2006 | Kemppainen et al. | |
| 7,156,880 B2 | 1/2007 | Evans et al. | |
| 7,166,133 B2 | 1/2007 | Evans et al. | |
| 7,189,263 B2 | 3/2007 | Erbe et al. | |
| 7,229,971 B2 | 6/2007 | Tanaka et al. | |
| 7,241,459 B2 | 7/2007 | Fechner et al. | |
| 7,531,004 B2 | 5/2009 | Bagga et al. | |
| 7,534,451 B2 | 5/2009 | Erbe et al. | |
| 7,544,212 B2 | 6/2009 | Li et al. | |
| 7,544,496 B2 | 6/2009 | Gower et al. | |
| 7,547,499 B2 | 6/2009 | Veregin et al. | |
| 7,578,845 B2 | 8/2009 | Nies et al. | |
| 7,621,963 B2 | 11/2009 | Simon et al. | |
| 8,252,055 B2 | 8/2012 | McKay | |
| 8,795,702 B2 | 8/2014 | Greenspan et al. | |
| 2002/0055143 A1 | 5/2002 | Bell et al. | |
| 2002/0112981 A1 | 8/2002 | Cooper et al. | |

(Continued)

FOREIGN PATENT DOCUMENTS

| | | |
|---|---|---|
| WO | WO98/46164 | 10/1998 |
| WO | WO 2010030964 A2 * | 3/2010 |
| WO | WO2013/188336 A2 | 12/2013 |

OTHER PUBLICATIONS

International Search Report completed Apr. 14, 2011 in International Application No. PCT/US2011/026961, filed Mar. 3, 2011.
English language translation of the International Preliminary Report on Patentability dated Sep. 4, 2012, from corresponding International Application No. PCT/US2011/026961, filed Mar. 3, 2011.
European Search Report received in Application No. 11751335.8 dated Jul. 7, 2014.
International Search Report received in PCT Application No. PCT/US14/32035 dated Aug. 20, 2014.
International Search Report and Written Opinion received in PCT Application No. PCT/US14/70633 dated Mar. 25, 2015.

*Primary Examiner* — Abigail Fisher
(74) *Attorney, Agent, or Firm* — Brinks Gilson & Lione (57) ABSTRACT

Compositions including crosslinked collagen and bioactive glass having an average pore size of at least 100 microns and methods of preparation thereof.

23 Claims, 2 Drawing Sheets

(56) References Cited

U.S. PATENT DOCUMENTS

| | | |
|---|---|---|
| 2004/0009598 A1 | 1/2004 | Hench et al. |
| 2005/0251267 A1 | 11/2005 | Winterbottom |
| 2008/0187571 A1 | 8/2008 | Clineff et al. |
| 2008/0221701 A1 | 9/2008 | Zhong et al. |
| 2010/0312355 A1 | 12/2010 | Yahav et al. |
| 2011/0217388 A1 | 9/2011 | Greenspan et al. |
| 2012/0035741 A1 | 2/2012 | Li et al. |
| 2013/0331898 A1 | 12/2013 | Nyemscek et al. |
| 2014/0017281 A1 | 1/2014 | Pomrink et al. |
| 2014/0231291 A1* | 8/2014 | Pomrink et al. ............... 206/438 |

* cited by examiner

IONICALLY CROSSLINKED MATERIALS AND METHODS FOR PRODUCTION

This application is a continuation-in-part of U.S. application Ser. No. 13/039,627, filed Mar. 3, 2011, which claims benefit of U.S. Provisional Application No. 61/310,129, filed Mar. 3, 2010, the entire contents of which is hereby incorporated herein by reference. This application also claims priority under 35 U.S.C. §119 to U.S. Provisional Patent Application No. 61/710,332, filed Oct. 5, 2012, the entire contents of which is hereby incorporated herein by reference.

BACKGROUND OF THE INVENTION

Collagen is the main component of connective tissue and is generally found in the body as a triple helix. Collagen is also prevalent in bone. Known methods of crosslinking include introducing disulfide bonds between individual collagen molecules and fibrils. Crosslinked collagen can have enhanced mechanical attributes. The addition of crosslinked collagen to wounded tissue or bone defects may serve to provide structural support. There are various ways to crosslink collagen, such as by UV light and the use of chemical crosslinkers. Herein is provided a novel way to crosslink collagen in a manner that maintains the sterility of collagen without introducing toxins that are difficult to remove.

Bioactive glass was originally developed in 1969 by L. Hench. Additionally bioactive glasses were developed as bone replacement materials, with studies showing that bioactive glass can induce or aid in osteogenesis. Hench et al, J. Biomed. Mater. Res. 5:117-141 (1971). Bioactive glass can form strong and stable bonds with bone. Piotrowski et al., J. Biomed. Mater. Res. 9:47-61 (1975). Further, bioactive glass is not considered toxic to bone or soft tissue from studies of in vitro and in vivo models. Wilson et al., J. Biomed. Mater. Res. 805-817 (1981). Exemplary bioactive glasses known in the art include 45S5, 45S5B1, 58S, and S70C30. The original bioactive glass, 45S5, is melt-derived. Sol-gel derived glasses have nanopores that allow for increased surface area and bioactivity.

U.S. Patent Application Publication No. 2002/0055143 discloses cement particles UV crosslinked with collagen.

U.S. Pat. No. 8,252,055 discloses crosslinking a collagen mineral containing composition including Bioglass.

BRIEF SUMMARY OF THE INVENTION

One aspect of the invention provides for a method for crosslinking collagen. An ion-containing solution is mixed with collagen and a glass to form a paste. The paste is freeze-dried to form a composite.

Another aspect of the invention provides for a method for crosslinking collagen fibers. Water or an ion-containing solution is mixed with collagen and a glass to form a paste. The paste is freeze-dried to form a composite. The composite is immersed in water or solutions containing divalent or polyvalent metal ions. The composite is freeze-dried.

Yet another aspect of the invention provides for a method for crosslinking collagen. An ion-containing solution is mixed with collagen and a glass to form a paste. The paste is transferred to a mold. The paste is freeze-dried to form a composite.

Another aspect of the invention provides for a method for crosslinking collagen fibers. Water or an ion-containing solution is mixed with collagen and a glass to form a paste. The paste is freeze-dried to form a composite. The composite is immersed in water or solutions containing divalent or polyvalent metal ions. The composite is freeze-dried and then dried.

An aspect provides for a mixture of collagen and a glass. The mixture comprises from 60 wt. % to 90 wt. % of the glass. The collagen is crosslinked by the glass. The mixture does not comprise chitosan or an organic crosslinking agent.

The invention also provides for a crosslinked collagen material consisting of collagen and a glass. Yet another aspect of the invention provides for a crosslinked collagen material consisting of collagen, water, and a glass. Alternatively, the invention provides for a crosslinked collagen material consisting of collagen, an ion-containing solution, and a glass.

The invention also provides for a crosslinked collagen material consisting of collagen fibers and a glass. Alternatively, the invention provides for a crosslinked collagen material consisting of collagen fibers, water, and a glass. Another aspect of the invention provides for a crosslinked collagen material consisting of collagen fibers, an ion-containing solution, and a glass.

DETAILED DESCRIPTION OF THE INVENTION

Figure 1:
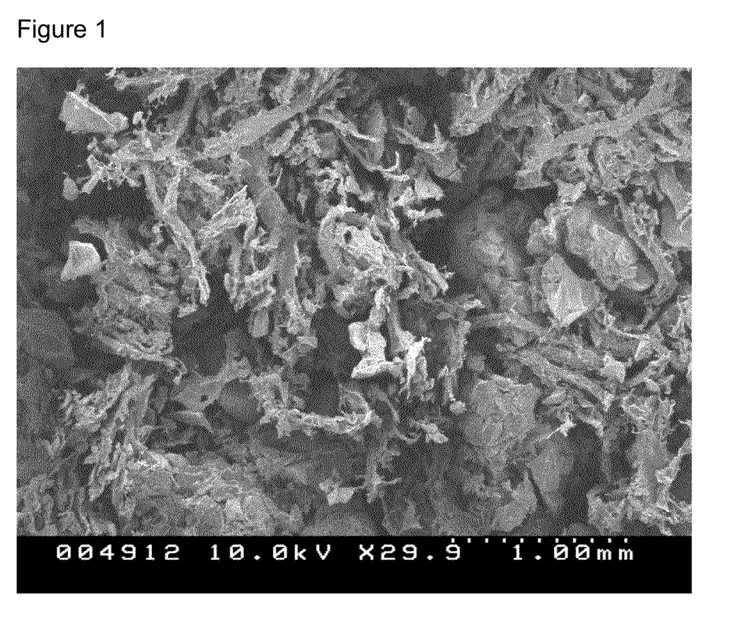
FIG. 1 is a photomicrograph of crosslinked collagen bioactive glass strip composite at 29.9× magnification.
Figure 2:
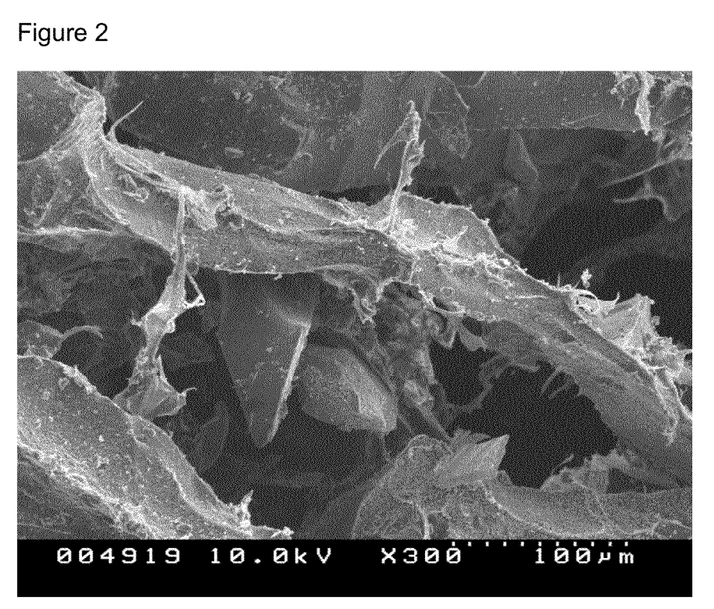
FIG. 2 is a photomicrograph of crosslinked collagen bioactive glass strip composite at 300× magnification.

One aspect of the invention provides for a method for crosslinking collagen. An ion-containing solution is mixed with the collagen and bioactive glass to form a paste. The paste is freeze-dried to form a composite. In some embodiments, the method further comprises drying the composite. These steps may be performed in succession or in any order. One way in which the composite may be dried is by dehydrothermal treatment. Significant crosslinking of the collagen can occur without any drying step or dehydrothermal treatment step undertaken. Addition of the drying step or dehydrothermal treatment step can lead to enhanced crosslinking.

Bioactive glass used in the invention may be melt-derived or sol-gel derived. Depending on their composition, bioactive glasses of the invention may bind to soft tissues, hard tissues, or both soft and hard tissues. The composition of the bioactive glass may be adjusted to modulate the degree of bioactivity. Furthermore, borate may be added to bioactive glass to control the rate of degradation. Additional elements, such as copper, zinc, and strontium may be added to bioactive glass to facilitate healthy bone growth. Bioactive glass that may also be suitable include glasses having about 40 to about 60 wt % $SiO_2$, about 10 to about 34 wt % $Na_2O$, up to about 20 wt % $K_2O$, up to about 5 wt % MgO, about 10 to about 35 wt % CaO, 0 to about 35 wt % SrO, up to about 20 wt % $B_2O_3$, and/or about 0.5 to about 12 wt % $P_2O_5$. The bioactive glass may additionally contain up to 10 wt % $CaF_2$. The bioactive glass may be in the form of a particle, a glass sheet, a fiber, a mesh, or any combination of these forms.

Bioactive glass is capable of bonding to bone, which begins with the exposure of bioactive glass to aqueous solutions. Sodium ions in the glass can exchange with hydronium ions in body fluids, which increases the pH. Calcium and phosphorous ions can migrate from the glass to form a calcium and phosphate-rich surface layer. Borate ions can also migrate from the glass to from a surface layer rich in boron. Strontium ions also can migrate from the glass to form a strontium-rich surface layer. Underlying this surface layer is another layer which becomes increasingly silica rich due to the loss of sodium, calcium, strontium, boron, and/or phosphate ions (U.S. Pat. No. 4,851,046). Hydrolysis may then disrupt the Si—O—Si bridges in the silica layer to form silanol groups, which can disrupt the glass network. The glass network is then thought to form a gel in which calcium phosphate from the surface layer accumulates. Mineralization may then occur as calcium phosphate becomes crystalline hydroxyapatite, which effectively mimics the mineral layer of bones.

Bioactive glass particles, fibers, meshes or sheets may be prepared by a sol-gel method. Methods of preparing such bioactive active glasses are described in Pereira, M. et al., "Bioactive glass and hybrid scaffolds prepared by sol-gel method for bone tissue engineering" Advances in Applied Ceramics, 2005, 104(1): 35-42 and in Chen, Q. et al., "A new sol-gel process for producing $Na_2O$-containing bioactive glass ceramics" Acta Biomaterialia, 2010, 6(10):4143-4153.

The composition can be allowed to solidify. In some embodiments, particles of bioactive glass are sintered to form a porous glass.

Repeated cooling and reheating may be performed on the solidified or sintered bioactive glass, with or without spinning, to draw the bioactive glass produced into fibers. A glass drawing apparatus may be coupled to the spinner and the source of molten bioactive glass, such as molten bioactive glass present in a crucible, for the formation of bioactive glass fibers. The individual fibers can then be joined to one another, such as by use of an adhesive, to form a mesh. Alternatively, the bioactive glass in molten form may be placed in a cast or mold to form a sheet or another desired shape.

The bioactive glass particles, fibers, meshes or sheets may further comprise any one or more of adhesives, grafted bone tissue, in vitro-generated bone tissue, collagen, calcium phosphate, stabilizers, antibiotics, antibacterial agents, antimicrobials, drugs, pigments, X-ray contrast media, fillers, and other materials that facilitate grafting of bioactive glass to bone.

A bioactive glass ceramic material suitable for the present compositions and methods may have silica, sodium, calcium, strontium, phosphorous, and boron present, as well as combinations thereof. In some embodiments, sodium, boron, strontium, and calcium may each be present in the compositions in an amount of about 1% to about 99%, based on the weight of the bioactive glass ceramic. In further embodiments, sodium, boron, strontium and calcium may each be present in the composition in about 1%, about 2%, about 3%, about 4%, about 5%, about 6%, about 7%, about 8%, about 9%, or about 10%. In certain embodiments, silica, sodium, boron, and calcium may each be present in the composition in about 5 to about 10%, about 10 to about 15%, about 15 to about 20%, about 20 to about 25%, about 25 to about 30%, about 30 to about 35%, about 35 to about 40%, about 40 to about 45%, about 45 to about 50%, about 50 to about 55%, about 55 to about 60%, about 60 to about 65%, about 65 to about 70%, about 70 to about 75%, about 75 to about 80%, about 80 to about 85%, about 85 to about 90%, about 90 to about 95%, or about 95 to about 99%. Some embodiments may contain substantially one or two of sodium, calcium, strontium, and boron with only traces of the other(s). The term "about" as it relates to the amount of calcium phosphate present in the composition means+/−0.5%. Thus, about 5% means 5+/−0.5%. Divalent cations or ions that may be present in any of the bioactive glasses of this and other aspects of the invention include one or more of iron-II, iron-III, alumina, chromate, cobalt, tin, copper, magnesium, and zinc.

The bioactive glass materials may further comprise one or more of a silicate, borosilicate, borate, strontium, or calcium, including SrO, CaO, $P_2O_5$, $SiO_2$, and $B_2O_3$. An exemplary bioactive glass is 45S5, which includes 46.1 mol % $SiO_2$, 26.9 mol % CaO, 24.4 mol % $Na_2O$ and 2.5 mol % $P_2O_5$. An exemplary borate bioactive glass is 45S5B1, in which the $SiO_2$ of 45S5 bioactive glass is replaced by $B_2O_3$. Other exemplary bioactive glasses include 58S, which includes 60 mol % $SiO_2$, 36 mol % CaO and 4 mol % $P_2O_5$, and S70C30, which includes 70 mol % $SiO_2$ and 30 mol % CaO. In any of these or other bioactive glass materials of the invention, SrO may be substituted for CaO.

The following composition, having a weight % of each element in oxide form in the range indicated, will provide one of several bioactive glass compositions that may be used to form a bioactive glass ceramic:

| | |
|---|---|
| $SiO_2$ | 0-86 |
| CaO | 4-35 |
| $Na_2O$ | 0-35 |
| $P_2O_5$ | 2-15 |
| $CaF_2$ | 0-25 |
| $B_2O_3$ | 0-75 |
| $K_2O$ | 0-8 |
| MgO | 0-5 |
| CaF | 0-35 |

In some embodiments, the particles are sintered to form porous particulate made from the bioactive glass particles. In one embodiment, fine particles of the bioactive glass are mixed with a sacrificial polymer and a binder to create a pre-shaped construct (e.g., a block or disk). The construct is then heated under specific conditions that allow a welding of the particles together without completely melting them. This process uses a temperature high enough to allow for the polymer material to burn off leaving a porous structure. The compression strength as well as the porosity of the construct may be controlled by varying the type and the amount of the sacrificial polymer and the sintering time and temperature used. Porosities as high as 90% may be achieved under suitable conditions. The pores in the bioactive glass material range from about 10 microns to about 5100 microns with an average pore size of 100±50 microns, 200±50 microns, 300±50 microns, 400±50 microns, 500±50 microns, 600±50 microns, 700±50 microns, 500-1000±50 microns or 1000-2000±50 microns.

The bioactive glass ceramic can be in the form of a three-dimensional compressible body of loose glass-based fibers in which the fibers comprise one or more glass-formers selected from the group consisting of $P_2O_5$, $SiO_2$, and $B_2O_3$. Some of the fibers have a diameter between about 100 nm and about 10,000 nm, and a length:width aspect ratio of at least about 10. The pH of the bioactive glass can be adjusted as-needed.

In any of the various aspects and embodiments of the invention, the bioactive glass may be in the form of a "CBG morsel", which as defined herein is a loose collagen and 45S5 bioactive glass mixture that becomes moldable when hydrated. Alternatively, in any of the various aspects and embodiments of the invention, the bioactive glass may be in the form of a "CBG strip", which as defined herein is collagen and 45S5 bioactive glass that is lyophilized into a rectangular shape.

In some embodiments, the body comprises fibers having a diameter between about 100 nm and about 10,000 nm. The especially small diameter of these fibers renders them highly flexible so they form into the compressible body without breaking. In some embodiments the body includes fibers meeting these dimensional requirements in addition to other glass morphologies, such as fibers of other dimensions, microspheres, particles, ribbons, flakes or the like. The fibers may have a variety of cross section shapes, such as flat, circular, oval, or non-circular.

Bioactive glass ceramics may be prepared by heating a composition comprising one or more of $SiO_2$, $CaH(PO_4)$, CaO, $P_2O$, $Na_2O$, $CaCO_3$, $Na_2CO_3$, $K_2CO_3$, MgO, and $H_2BO_3$ to a temperature between 1300 and 1500° C. such that the composition may form molten glass. An exemplary composition that can form fibers includes 40-60% $SiO_2$, 10-20% CaO, 0-4% $P_2O_5$, and 19-30% NaO. Other exemplary compositions include 45S5, which includes 46.1 mol % $SiO_2$, 26.9 mol % Ca), 24.4 mol % $Na_2O$ and 2.5 mol % $P_2O_5$; 45S5B1, which includes 46.1 mol % $B_2O_3$, 26.9 mol % Ca), 24.4 mol % $Na_2O$ and 2.5 mol % $P_2O_5$; 58S, which includes 60 mol % $SiO_2$, 36 mol % CaO and 4 mol % $P_2O_5$; and S70C30, which includes 70 mol % $SiO_2$ and 30 mol % CaO. Another exemplary composition includes 40 mol % $SiO_2$, 40 mol % $B_2O_3$, 20 mol % CaO, and 20 mol % $Na_2O$.

In this and other aspects of the invention, dehydrothermal treatment may involve the removal of water from collagen. Various methods of dehydrothermal treatment of collagen are known in the art. Dehydrothermal treatment generally involves application of moderate heat under vacuum to remove water from the collagen. Crosslinking can result from dehydrothermal treatment by a dehydration reaction in which a hydroxyl group from one collagen molecule is combined with a proton from another collagen molecule. It is noted that in the various aspects and embodiments of the invention, significant crosslinking of the collagen can occur without dehydrothermal treatment.

In some embodiments, the steps are carried out in succession as follows. Water or an ion-containing solution is first mixed with the collagen and bioactive glass to form a paste. The paste is then freeze-dried to form a composite. Then, the composite is dried, such as by dehydrothermal treatment. It is noted that significant crosslinking of the collagen can occur without any drying step or dehydrothermal treatment step undertaken.

Optional soaking steps may be undertaken before and/or after one or more of each of the lyophilization, freeze-drying or dehydrothermal treatments. The bioactive glass, collagen, pastes, and/or composites may be soaked in solutions that include water, PBS, $Fe_2(SO_4)_3$, or any other suitable buffer.

The collagen is in the form of fibers suspended in aqueous solution. In some embodiments, the bioactive glass is present in a weight ratio of from 80% to 90% in proportion to the total weight of the bioactive glass and the collagen. The weight ratio of bioactive glass may be about 80%, about 81%, about 82%, about 83%, about 84%, about 85%, about 86%, about 87%, about 88%, about 89%, or about 90% in proportion to the total weight of the bioactive glass and the collagen.

In some embodiments of this and other aspects of the invention, the composite is ionically-crosslinked. Incubation of collagen in a solution containing divalent cations is effective to crosslink collagen. The divalent cations can be one or more of $Ca^{2+}$, $Mg^{2+}$, $Fe^{2+}$, $Sr^{2+}$, $Cd^{2+}$, $Co^{2+}$, $Mn^{2+}$, $Ni^{2+}$, and $Zn^{2+}$. The divalent cations may be leached from glass that is submerged in water or an aqueous ion-containing solution. For example, a bioactive glass submerged in water can leach calcium and/or strontium ions.

In some embodiments of this and other aspects of the invention, the mechanical properties of the composite, or material, are tested. For instance, the tensile strength may be measured, for example, if the composite is in the form of fibers. Methods of measuring tensile strength are known in the art, such as described in ASTM-D 638, which is incorporated by reference herein in its entirety. The compressive strength, or ability of the composite or material to resist compression, may also be measured. Methods of measuring compressive strength are known in the art, such as described in ASTM-D 695, which is incorporated by reference herein in its entirety. Also, the flexural strength of the material may be tested, such as described in Goudouri, et al., "Dental Ceramics/Bioactive Glass Composites: Characterization and Mechanical Properties Investigation" Bioceramics Dev. App. 2011, (1):1-4, incorporated by reference in its entirety herein.

Another aspect of the invention provides for a method for crosslinking collagen. Water or an ion-containing solution is mixed with collagen and a glass to form a paste. The paste is freeze-dried to form a composite. The method may further comprise drying the composite, such as by dehydrothermal treatment. The dehydrothermal treatment step is not required, however, for significant crosslinking to occur. These steps may be performed in succession or in any order. The glass may be such that it is capable of releasing divalent cations in the presence of water. Some exemplary glasses include a blend of ionomer glass with a 45S5 bioactive glass and a slurry of a 1% $CaCl_2$ solution at pH 6.5 with a 45S5 bioactive glass. If the glass releases divalent cations, these may be one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$.

In some embodiments, the steps are carried out in succession as follows. Water or an ion-containing solution is first mixed with collagen and a glass to form a paste. The paste is then freeze-dried to form a composite. After freeze-drying, the composite may optionally be dried, such as by dehydrothermal treatment. The dehydrothermal treatment step is not required, however, for significant crosslinking to occur.

Optional soaking steps may be undertaken before and/or after one or more of each of the lyophilization, freeze-drying, or dehydrothermal treatments. The bioactive glass, collagen, pastes, and/or composites may be soaked in solutions that include water, PBS, $Fe_2(SO_4)_3$, or any other suitable buffer.

In some embodiments, collagen is in the form of collagen fibers suspended in aqueous solution.

The composite formed in any of the embodiments of this aspect may be ionically-crosslinked. The ionic crosslinking can occur by means of the various methods and embodiments described herein, such as by incubating the composite in bioactive glass. In some embodiments, the composite comprises from 60 wt. % to 90 wt. % of the glass, from 65 wt. % to 90 wt. % of the glass, from 70 wt. % to 90 wt. % of the glass, from 75 wt. % to 90 wt. % of the glass, or from 80 wt. % to 90 wt. % of the glass. In some embodiments, the weight ratio of the bioactive glass in the composite may be about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90%.

Another aspect of the invention provides for a method for crosslinking collagen fibers. Water or an ion-containing solution is mixed with collagen and a glass to form a paste. The paste is freeze-dried to form a composite. The composite is immersed in water or solutions containing divalent or polyvalent metal ions. The immersion may be from 3 to 24 hours. The composite is freeze-dried. In some embodiments, collagen is in the form of fibers suspended in aqueous solution. These steps may be performed in succession or in any order.

The method may further comprise drying the composite, such as by dehydrothermal treatment. The dehydrothermal treatment step is not required, however, for significant crosslinking to occur. In some embodiments, the glass is capable of releasing divalent cations in the presence of water. Some exemplary divalent cations include one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$. The glass may be a bioactive glass. The composite may be ionically-crosslinked.

Optional soaking steps may be undertaken before and/or after one or more of each of the lyophilization, freeze-drying or dehydrothermal treatments. The bioactive glass, collagen, pastes, and/or composites may be soaked in solutions that include water, PBS, $Fe_2(SO_4)_3$, or any other suitable buffer.

In some embodiments, the composite comprises from 60 wt. % to 90 wt. % of the glass, from 65 wt. % to 90 wt. % of the glass, from 70 wt. % to 90 wt. % of the glass, from 75 wt. % to 90 wt. % of the glass, or from 80 wt. % to 90 wt. % of the glass. In some embodiments, the weight ratio of the bioactive glass in the composite may be about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90%.

Another aspect of the invention provides for a method for crosslinking collagen fibers. Water or an ion-containing solution is mixed with collagen and a glass to form a paste. The paste is freeze-dried to form a composite. The composite is immersed in water or solutions containing divalent or polyvalent metal ions. The composite is freeze-dried and then dried. These steps may be performed in succession or in any order.

In some embodiments of this aspect, the method further comprises drying the composite. The drying may be conducted by dehydrothermal treatment. The dehydrothermal treatment step is not required, however, for significant crosslinking to occur. In some embodiments, the glass is capable of releasing divalent cations in the presence of water. Some exemplary divalent cations include one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$.

In some embodiments, the glass is a bioactive glass, such as those described in the above aspect of the invention.

In some embodiments, the mechanical properties of the composite are tested. The ways in which mechanical properties are tested include those discussed in other aspects of the invention.

In some embodiments, collagen is in the form of collagen fibers suspended in aqueous solution.

In some embodiments, the immersion of the composite in water or solutions containing divalent or polyvalent metal ions is conducted from 3 to 24 hours. The immersion may be conducted for about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours.

In some embodiments of this aspect, the composite is ionically-crosslinked by any of the various methods described herein, such as by incubating the composite in a solution having divalent cations. An exemplary solution is calcium chloride. The calcium chloride may be in a concentration ranging from 0.1% to 1%, such as 0.1%, 0.2%, 0.25%, 0.3%, 0.4%, 0.5%, 0.6%, 0.7%, 0.8%, 0.9%, and 1.0%. The calcium chloride solution may be at any pH, such as pH 6.5 or pH 7.0. Crosslinking may also be enhanced by adding ionomer glass, such as TF-325 in powder form.

Optional soaking steps may be undertaken before and/or after one or more of each of the lyophilization or dehydrothermal treatments. The bioactive glass, collagen, pastes, and/or composites may be soaked in solutions that include water, PBS, $Fe_2(SO_4)_3$, or any other suitable buffer.

In some embodiments of this aspect, the composite comprises from 60 wt. % to 90 wt. % of the glass, from 65 wt. % to 90 wt. % of the glass, from 70 wt. % to 90 wt. % of the glass, from 75 wt. % to 90 wt. % of the glass, or from 80 wt. % to 90 wt. % of the glass. In some embodiments, the weight ratio of the bioactive glass in the composite may be about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90%.

Yet another aspect of the invention provides for a method for crosslinking collagen. An ion-containing solution is mixed with collagen and a glass to form a paste. The paste is transferred to a mold. The paste is freeze-dried to form a composite.

In some embodiments of this aspect, the method further comprises drying the composite. The drying may be conducted by dehydrothermal treatment. The dehydrothermal treatment step is not required, however, for significant crosslinking to occur. In some embodiments, the glass is capable of releasing divalent cations in the presence of water. Some exemplary divalent cations include one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$.

In some embodiments, the glass is a bioactive glass. The bioactive glass may be one or more of the various bioactive glasses described herein. In some embodiments, the bioactive glass may be 45S5. Crosslinking may also be enhanced by adding ionomer glass, such as TF-325 in powder form.

Optional soaking steps may be undertaken before and/or after one or more of each of the lyophilization, freeze-drying or dehydrothermal treatments. The bioactive glass, collagen, pastes, and/or composites may be soaked in solutions that include water, PBS, $Fe_2(SO_4)_3$, or any other suitable buffer.

In some embodiments, the mechanical properties of the composite are tested. The ways in which mechanical properties are tested include those discussed in other aspects of the invention.

The collagen may be in the form of collagen fibers suspended in aqueous solution.

In some embodiments, the immersion of the composite in water or solutions containing divalent or polyvalent metal ions is conducted from 3 to 24 hours. The immersion may be conducted for about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours.

In some embodiments of this aspect, the composite is ionically-crosslinked. The crosslinking may arise from the presence of divalent cations, as discussed above.

In some embodiments of this aspect, the composite comprises from 60 wt. % to 90 wt. % of the glass, from 65 wt. % to 90 wt. % of the glass, from 70 wt. % to 90 wt. % of the glass, from 75 wt. % to 90 wt. % of the glass, or from 80 wt. % to 90 wt. % of the glass. In some embodiments, the weight ratio of the bioactive glass in the composite may be about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90%.

The invention also provides for a mixture of collagen and a glass. The mixture comprises from 60 wt. % to 90 wt. % of the glass. The collagen is crosslinked by the glass. The mixture does not comprise chitosan or an organic crosslinking agent. In some embodiments of this aspect, the mixture further comprises water. The glass may be capable of releasing divalent cations in the presence of water. In some embodiments, the divalent cations released include one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$. In some embodiments, the glass is a bioactive glass.

In some embodiments of this aspect, the composite comprises from 60 wt. % to 90 wt. % of the glass, from 65 wt. % to 90 wt. % of the glass, from 70 wt. % to 90 wt. % of the glass, from 75 wt. % to 90 wt. % of the glass, or from 80 wt. % to 90 wt. % of the glass. In some embodiments, the weight ratio of the bioactive glass in the composite may be about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90%.

In some embodiments, the glass is capable of releasing divalent cations in the presence of water. The divalent cations may be one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$. The glass may be a bioactive glass in some embodiments of this aspect as well. Crosslinking may also be enhanced by adding ionomer glass, such as TF-325 in powder form.

Another aspect of the invention provides for a crosslinked collagen material consisting of collagen and a glass. The material comprises from 60 wt. % to 90 wt. % of the glass. In any of the embodiments of this aspect, the material comprises about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% of the glass by weight.

In some embodiments, the glass is capable of releasing divalent cations in the presence of water. The divalent cations may be one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$. The glass may be a bioactive glass in some embodiments of this aspect as well.

Yet another aspect of the invention provides for a crosslinked collagen material consisting of collagen, water, and a glass. The material may comprise from 60 wt. % to 90 wt. % of the glass. Alternatively, the material may comprise from 65 wt. % to 90 wt. % of the glass, from 70 wt. % to 90 wt. % of the glass, from 75 wt. % to 90 wt. % of the glass, or from 80 wt. % to 90 wt. % of the glass. In any of the embodiments of this aspect, the material comprises about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% of the glass by weight.

In some embodiments, the glass is capable of releasing divalent cations in the presence of water. The divalent cations may be one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$. The glass may be a bioactive glass in some embodiments of this aspect as well. Crosslinking may also be enhanced by adding ionomer glass, such as TF-325 in powder form.

Optional soaking steps may be undertaken before and/or after one or more of each of the lyophilization, freeze-drying or dehydrothermal treatments. The bioactive glass, collagen, pastes, and/or composites may be soaked in solutions that include water, PBS, $Fe_2(SO_4)_3$, or any other suitable buffer.

Yet another aspect of the invention provides for a crosslinked collagen material consisting of collagen, water, ions, and a glass. The material comprises from 60 wt. % to 90 wt. % of the glass. Alternatively, the material may comprise from 65 wt. % to 90 wt. % of the glass, from 70 wt. % to 90 wt. % of the glass, from 75 wt. % to 90 wt. % of the glass, or from 80 wt. % to 90 wt. % of the glass. In any of the embodiments of this aspect, the material comprises about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% of the glass by weight.

In some embodiments, the glass is capable of releasing divalent cations in the presence of water. The divalent cations may be one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$. The glass may be a bioactive glass in some embodiments of this aspect as well.

Another aspect of the invention provides for a crosslinked collagen material consisting of collagen fibers and a glass. The material comprises from 60 wt. % to 90 wt. % of the glass. Alternatively, the material may comprise from 65 wt. % to 90 wt. % of the glass, from 70 wt. % to 90 wt. % of the glass, from 75 wt. % to 90 wt. % of the glass, or from 80 wt. % to 90 wt. % of the glass. In any of the embodiments of this aspect, the material comprises about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% of the glass by weight.

In some embodiments, the glass is capable of releasing divalent cations in the presence of water. The divalent cations may be one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$. The glass may be a bioactive glass as well.

Yet another aspect of the invention provides for a crosslinked collagen material consisting of collagen fibers, water, and a glass. The material comprises from 60 wt. % to 90 wt. % of the glass. Alternatively, the material may comprise from 65 wt. % to 90 wt. % of the glass, from 70 wt. % to 90 wt. % of the glass, from 75 wt. % to 90 wt. % of the glass, or from 80 wt. % to 90 wt. % of the glass. In any of the embodiments of this aspect, the material comprises about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% of the glass by weight.

In some embodiments, the glass is capable of releasing divalent cations in the presence of water. The divalent cations may be one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$. The glass may also be a bioactive glass.

Another aspect of the invention provides for a crosslinked collagen material consisting of collagen fibers, water, ions, and a glass. The material comprises from 60 wt. % to 90 wt. % of the glass.

The material comprises from 60 wt. % to 90 wt. % of the glass. Alternatively, the material may comprise from 65 wt. % to 90 wt. % of the glass, from 70 wt. % to 90 wt. % of the glass, from 75 wt. % to 90 wt. % of the glass, or from 80 wt. % to 90 wt. % of the glass. In any of the embodiments of this aspect, the material comprises about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% of the glass by weight.

In some embodiments, the glass is capable of releasing divalent cations in the presence of water. The divalent cations may be one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$. The glass may be a bioactive glass in some embodiments of this aspect as well.

Example 1

Preparation of CBG Morsels

A "CBG morsel" as defined herein is a loose collagen and 45S5 bioactive glass mixture that becomes moldable when hydrated.

The control sample "1" was prepared by hydrating 100% collagen with HIGH PURITY WATER (deionized water prepared using the Sartorius system) until the material became moldable and then by forming a 2.5 cc sphere. The sphere was then soaked in HIGH PURITY WATER for 24 hours.

The test samples "2", "3", and "4" were prepared by combining 1-2 mm, 90-710 μm 45S5 bioglass, and 32-125 μm 45S5 bioglass with collagen. The dry materials were then hydrated with varying $CaCl_2$ solutions and then soaked in HIGH PURITY WATER for 24 hours.

Test samples "5" and "7" were prepared similarly to Samples 2-4 except HCl was used to adjust the pH of the different percent $CaCl_2$ solutions to 6.5.

Test sample "6" was prepared by replacing 5 wt % of the 32-125 μm 45S5 bioactive glass with ionomer glass, in particular ionomer glass powder TF-325. The morsel was then hydrated and soaked in HIGH PURITY WATER.

The samples were evaluated on the Shimadzu Mechanical Strength Tester using compressive plates and a 1 kN Load cell. Tests were conducted under ambient conditions and all samples were tested in accordance with SOP PR-06.06 Mechanical Testing of CBG Product. The indenter displacement was set to 25 mm with a rate of 15 mm/min. The load was released when a max strength of 900 N or a max stroke of 30 mm was obtained.

The following table illustrates the composition and the compressive strength of the CBG Morsel samples that were evaluated.

| | Dry Composition (wt %) | | | Size | Hydrating | Soaking | Compressive Strength |
|---|---|---|---|---|---|---|---|
| ID | Collagen | Bioglass | Misc. | (cc) | Soln. | Soln. | (kPa) |
| 1 | 100 | 0 | 0 | 2.5 | RODI | RODI | 7.22424 |
| 2 | 15 | 85 | 0 | 2.5 | 0.1% $CaCl_2$ | RODI | 37.5007 |
| 3 | 15 | 85 | 0 | 2.5 | 0.25% $CaCl_2$ | RODI | 51.3565 |
| 4 | 15 | 85 | 0 | 2.5 | 1% $CaCl_2$ | RODI | 63.7604 |
| 5 | 15 | 85 | 0 | 2.5 | 0.5% $Ca(Cl)_2$ pH 6.5 | RODI | 105.645 |
| 6 | 15 | 80 | 5% Ionomer Glass | 2.5 | RODI | RODI | 128.284 |
| 7 | 15 | 85 | 0 | 2.5 | 1% $Ca(Cl)_2$ pH 6.5 | RODI | 148.51 |

The data in Table 1 indicates that after soaking, morsels containing bioactive glass are stronger than a morsel containing only collagen (control sample 1). The data for test samples 3-5 and 7 indicates that the increasing concentration of $Ca^{2+}$ ions in the hydration solution increases the compressive strength. Test sample 6 was prepared with the same hydrating and soaking solutions as the control (sample 1) and exhibited higher compressive strength because of the presence of the bioactive and ionomer glasses.

Samples prepared with bioglass and hydrated with various calcium chloride solutions exhibited ionic crosslinking when soaked for 24 hours in HIGH PURITY WATER.

Example 2

Preparation of CBG Strips

A "CBG strip" as defined herein is collagen and 45S5 bioactive glass that is lyophilized into a rectangular shape.

The control Sample A was prepared by making a slurry with collagen and HIGH PURITY WATER in a 1:1 ratio by weight. The slurry was then lyophilized and subjected to DHT in molds to form 5 cc strips. The collagen strips were then soaked in HIGH PURITY WATER for 3 hours and lyophilized once more.

Test Sample B was prepared similarly to Sample A, except the soaking solution following DHT was 1% $Fe_2(SO_4)_3$ in place of HIGH PURITY WATER.

Test Samples C and E were prepared with a slurry of glass, collagen, and HIGH PURITY WATER adjusted to a pH of 5. Sample C contained 90 wt % glass and Sample E contained 85 wt % glass. The slurries were then lyophilized and then subjected to DHT to form strips, soaked in HIGH PURITY WATER for 3 hours and lyophilized once more.

Test Sample D was prepared similarly to sample E except the slurry solution was pH adjusted $CaCl_2$ in place of HIGH PURITY WATER and HCl and the soaking solution was PBS in place of HIGH PURITY WATER.

Test Sample F was prepared by combining the glass and collagen, hydrating with HIGH PURITY WATER, and placing the sample into the tray. The tray was then soaked in HIGH PURITY WATER for 3 hours and lyophilized. Sample E did not undergo DHT.

A "plate" shape was used to evaluate the strips on the Shimadzu Mechanical Strength Tester. Tests were conducted under ambient conditions and all samples were tested in accordance with SOP PR-06.06 Mechanical Testing of CBG Product. Stress was applied in a circumferential direction. Specimens were elongated at a rate of 5 mm/min until failure, with the force and extension recorded over time.

The following table illustrates the composition and the tensile strength of the CBG Strip samples that were evaluated. Sample A is the control.

| | Composition | | | | | | | Tensile |
|---|---|---|---|---|---|---|---|---|
| ID | Collagen % wt | 32-125 um % wt | 710-90 um % wt | 1-2 mm % wt | Slurry Prep | Lyo | DHT | Soaking Soln. | Strength (kPa) |
| A | 100 | 0 | 0 | 0 | RODI | Twice | Once | RODI | 4.24 |
| B | 100 | 0 | 0 | 0 | RODI | Twice | Once | 1% $Fe_2(SO_4)_3$ | 7.93 |
| C | 10 | 15 | 15 | 60 | RODI + HCl | Twice | Once | RODI | 14.37 |
| D | 15 | 12.5 | 12.5 | 60 | $Ca(Cl)_2$ pH 6.5 | Twice | Once | PBS | 14.87 |
| E | 15 | 12.5 | 12.5 | 60 | RODI + HCl | Twice | Once | RODI | 26.7 |
| F | 15 | 12.5 | 12.5 | 60 | RODI | Once | None | RODI | 28.93 |

The following bulk densities were obtained for CBG strips:

| Collagen Bioglass Ionically Crosslinked Composite (5 cc samples) | | |
|---|---|---|
| | Mass (g) | Bulk Density (g/cc) |
| 1 | 3.547 | 0.7094 |
| 2 | 3.582 | 0.7164 |
| 3 | 3.915 | 0.783 |
| 4 | 3.526 | 0.7052 |
| 5 | 3.455 | 0.691 |
| 6 | 3.594 | 0.7188 |
| 7 | 3.856 | 0.7712 |
| Avg. | 3.639 | 0.7279 |
| Std. Dev. | 0.175 | 0.0350 |
| % Porosity: 30-70% | | |
| Bulk Density: less than 1 g/cc | | |

The control Sample A, was crosslinked using DHT processing. Therefore the increased tensile properties observed in the other Samples B through F can be attributed to ionic crosslinking. The tensile strength of Sample B when compared to the control indicates that ionic crosslinking occurred between the $Fe^{3+}_{(aq)}$ and the collagen fibers. Samples C and E exhibited higher tensile strengths than the control (Sample A). The compressive strength of Sample F indicates that CBG Strips can be crosslinked without DHT processing.

Samples prepared with bioglass exhibited greater tensile strength than the control that was only crosslinked with DHT. Sample F indicates that the collagen can be crosslinked and a high tensile strength can be achieved without DHT processing.

Throughout this specification various indications have been given as preferred and alternative embodiments of the invention. However, the foregoing detailed description is to be regarded as illustrative rather than limiting and the invention is not limited to any one of the preferred embodiments. It should be understood that it is the appended claims, including all equivalents, that are intended to define the spirit and scope of this invention.

The invention claimed is:

1. A method for preparing a collagen bioglass ionically cross-linked composite, comprising:
   mixing water or an ion-containing solution of divalent or polyvalent metal ions with the collagen and bioactive glass having an average pore size of at least 100 microns for a time sufficient to cross-link collagen and to form a paste, wherein the mixture comprises from 60 wt. % to 98 wt. % of bioactive glass, and the collagen is crosslinked by the bioactive glass or divalent or polyvalent metal ions; and
   freeze-drying the paste to form the collagen bioactive glass ionically cross-linked composite,
   wherein the method does not utilize chitosan or an organic crosslinking agent; and
   wherein the paste is free of calcium phosphate.

2. The method of claim 1, wherein the bioactive glass is present in at least 80% in proportion to the total weight of the bioactive glass and the collagen.

3. The method of claim 1, wherein the collagen is in the form of collagen fibers suspended in an aqueous solution.

4. A method for preparing a collagen bioglass ionically cross-linked composite consisting comprising:
   mixing water or an ion-containing solution of divalent or polyvalent metal ions with the collagen and a bioactive glass to form a paste, wherein the mixture comprises from 60 wt. % to 98 wt. % of the bioactive glass;
   freeze-drying the paste to form the composite;
   immersing the composite in water or the ion-containing solution of divalent or polyvalent metal ions for a time sufficient to cross-link collagen and to form a paste; and
   freeze-drying the composite,
   wherein the method does not utilize chitosan or an organic cross-linking agent; and
   wherein the paste is free of calcium phosphate.

5. The method of claim 4, wherein the divalent or polyvalent metal ions are one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$ and $Zn^{2+}$.

6. The method of claim 4, wherein the immersing is conducted from 3 to 24 hours.

7. The method of claim 4, wherein the composite comprises from 60 wt. % to 90 wt. % of the glass.

8. The method of claim 4, wherein the composite comprises from 65 wt. % to 90 wt. % of the glass.

9. The method of claim 4, wherein the composite comprises from 70 wt. % to 90 wt. % of the glass.

10. A mixture of collagen fibers and a glass, wherein the mixture comprises from 60 wt. % to 90 wt. % of the glass and wherein the collagen fibers are crosslinked by the glass, with the proviso that the mixture does not comprise chitosan or an organic crosslinking agent.

11. The mixture of claim 10, further comprising water or an ion-containing solution.

12. The mixture of claim 10, wherein the glass is capable of releasing divalent cations in the presence of water.

13. The mixture of claim 10, wherein the divalent or polyvalent metal ions are one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$ and $Zn^{2+}$.

14. The mixture of claim 10, wherein the glass is a bioactive glass.

15. The mixture of claim 10, wherein the mixture comprises from 65 wt. % to 90 wt. % of the glass.

16. The mixture of claim 10, wherein the mixture comprises from 70 wt. % to 90 wt. % of the glass.

17. The mixture of claim 10, wherein the mixture comprises from 75 wt. % to 90 wt. % of the glass.

18. The mixture of claim 10, wherein the mixture comprises from 80 wt. % to 90 wt. % of the glass.

19. A crosslinked collagen material consisting of collagen and a bioactive glass, wherein the material comprises from 60 wt % to 90 wt. % of the bioactive glass, and the glass has an average pore size of at least 100 microns.

20. The material of claim 19, wherein the material comprises from 65 wt. % to 90 wt. % of the glass.

21. The material of claim 19, wherein the material comprises from 70 wt. % to 90 wt. % of the glass.

22. The material of claim 19, wherein the material comprises from 75 wt. % to 90 wt. % of the glass.

23. The material of claim 19, wherein the material comprises from 80 wt. % to 90 wt. % of the glass.

* * * * *